United States Patent
Schmidt et al.

(10) Patent No.: US 6,815,119 B2
(45) Date of Patent: Nov. 9, 2004

(54) TETRAKISFLUOROALKYLBORATE SALTS AND THEIR USE AS CONDUCTING SALTS

(75) Inventors: Michael Schmidt, Seeheim-Jugenheim (DE); Andreas Kuehner, Darmstadt (DE); Helge Willner, Muehlheim/Ruhr (DE); Eduard Bernhardt, Duisburg (DE)

(73) Assignee: Merck Patent GmbH, Darmstadt (DE)

( * ) Notice: Subject to any disclaimer, the term of this patent is extended or adjusted under 35 U.S.C. 154(b) by 200 days.

(21) Appl. No.: 09/986,770

(22) Filed: Nov. 9, 2001

(65) Prior Publication Data

US 2002/0090547 A1 Jul. 11, 2002

(30) Foreign Application Priority Data

Nov. 10, 2000  (DE) .......................................... 100 55 811

(51) Int. Cl.$^7$ .......................... H01M 6/04; H01M 6/18; H01G 9/02; C07F 5/06; C07F 9/06
(52) U.S. Cl. ....................... 429/188; 429/307; 429/313; 429/314; 429/317; 361/527; 556/172; 556/175; 556/176; 556/187
(58) Field of Search ................................. 429/307, 313, 429/314, 317, 188; 361/527; 556/172, 175, 176, 187

(56) References Cited

U.S. PATENT DOCUMENTS

| | | | | |
|---|---|---|---|---|
| 3,884,723 A | * | 5/1975 | Wuttke ........................ | 429/162 |
| 4,505,997 A | | 3/1985 | Armand et al. ............. | 429/192 |
| 5,273,840 A | | 12/1993 | Dominey .................... | 429/192 |
| 6,500,575 B1 | * | 12/2002 | Shiue et al. ................. | 429/27 |
| 2002/0028389 A1 | * | 3/2002 | Sonoda et al. .............. | 429/324 |

FOREIGN PATENT DOCUMENTS

| | | |
|---|---|---|
| DE | 10027 626 A1 | 6/2000 |
| DE | 19922522 A1 | 11/2000 |
| DE | 19932317 A1 | 1/2001 |
| DE | 19946066 A1 | 3/2001 |
| DE | 19953051 A1 | 4/2001 |
| DE | 10042149 A1 | 5/2001 |
| DE | 19951804 A1 | 5/2001 |
| DE | 19959722 A1 | 6/2001 |
| DE | 10008955 A1 | 9/2001 |
| DE | 10014884 A1 | 9/2001 |
| DE | 19941 566 A1 | 9/2001 |
| DE | 10016024 A1 | 10/2001 |
| DE | 10016801 A1 | 10/2001 |
| DE | 10025761 A1 | 11/2001 |
| DE | 10025762 A1 | 11/2001 |
| DE | 10026565 A1 | 12/2001 |
| DE | 10027995 A1 | 12/2001 |
| EP | 1 127 888 A1 | 8/2001 |
| EP | 1 174 941 A2 | 1/2002 |
| EP | 1 229 038 A1 | 8/2002 |

OTHER PUBLICATIONS

Chemistry of Nonaqueous Solutions, Current Progress, 1994 VCH Publishers, Inc., 4 pgs.

Nonaqueous Electrochemistry, Marcel Dekker, Inc., 3 pgs.

Handbook Of Batteries, McGraw–Hill, Inc., 9 pgs.

E. Bernhardt, G. Henkel, H. Willner, Die Tetracyanoborate M[B(CN)$_4$], M=[Bu$_4$N]$^+$, Ag$^+$, K$^+$, Z. Anorg. Allg. Chem. 2000, 626, 560–580.

* cited by examiner

Primary Examiner—Patrick Ryan
Assistant Examiner—Thomas H. Parsons
(74) Attorney, Agent, or Firm—Millen White Zelano & Branioan P.C.

(57) ABSTRACT

The present invention relates to tetrakisfluoroalkylborate salts, methods of producing same, and their use in electrolytes, batteries, capacitors, supercapacitors, and galvanic cells.

50 Claims, No Drawings

TETRAKISFLUOROALKYLBORATE SALTS AND THEIR USE AS CONDUCTING SALTS

The present invention relates to tetrakisfluoroalkylborate salts, methods of producing same, and their use in electrolytes, batteries, capacitors, supercapacitors, and galvanic cells.

In recent years, the spreading of portable electronic devices such as laptop and palmtop computers, cell telephones, or video cameras and thus, the demand for light-weight and high-performance batteries has dramatically increased worldwide.

In view of such rapidly increasing demand for batteries and the associated ecological problems, the development of rechargeable batteries having long service life has become more and more important.

Starting in the early nineties, rechargeable lithium ion batteries have been traded commercially. Most of these batteries work with lithium hexafluorophosphate as conducting salt. However, this lithium salt is a compound which is extremely sensitive to hydrolysis and has low thermal stability and therefore, due to such properties of this salt, appropriate batteries can only be produced by means of highly expensive and thus, exceedingly cost-intensive processes. Also, the sensitivity of this lithium salt reduces the service life and the performance of such lithium batteries, impairing their use under extreme conditions, such as high temperatures.

Therefore, numerous attempts have been made to provide lithium salts having improved properties. Thus, U.S. Pat. Nos. 4,505,997 and 5,273,840 describe the use of lithium [tris(trifluoromethylsulfonyl)imide] or lithium [tris(trifluoromethylsulfonyl)methanide] salts as conducting salts in batteries. Both of these salts have high anodic stability, forming solutions of high conductivity with organic carbonates. However, lithium bis(trifluoromethylsulfonyl)imide has the drawback of insufficient passivation of the aluminum metal functioning as cathodic current conductor in lithium batteries. On the other hand, the production and purification of lithium tris(trifluoromethylsulfonyl)methanide is only possible with exceedingly high efforts, so that the use of this salt as conducting salt in batteries massively increases the production cost of such lithium batteries.

Another lithium salt used in battery cells is lithium tetrafluoroborate. However, this salt has a relatively low solubility in most solvents, so that solutions thereof generally have low ionic conductivities.

It is therefore the object of the present invention to provide conducting salts that would exhibit no or only slight evidence of hydrolytic decomposition over a long period of time. Furthermore, these conducting salts also should have high ionic conductivity, high thermal stability and from good to very good solubility in usual solvents. Another object of the present invention is to improve or enhance the service life and performance of primary and secondary batteries, capacitors, supercapacitors and/or galvanic cells.

Said object is accomplished by providing tetrakisfluoroalkylborate salts of general formula (I)

$$M^{n+}([BR_4]^-)_n \quad (I)$$

wherein $M^{n+}$ is a univalent, bivalent, or trivalent cation, each of the ligands R are the same and straight-chained or branched and represent $(C_xf_{2x+1})$, with $1 \leq x \leq 8$, and $n=1$, 2 or 3.

Preferred are those tetrakisfluoroalkylborate salts of the invention having the general formula (I), wherein $MM^{n+}$ is an alkali metal cation, preferably a lithium, sodium or potassium cation, and more preferably a lithium cation, a magnesium or aluminum cation.

Furthermore, those tetrakisfluoroalkylborate salts of general formula (I) are preferred wherein the $M^{n+}$ cation is an organic cation, preferably a nitrosyl cation, a nitryl cation, or a cation of general formula $[N(R^7)_4]^+$, $[P(N(R^7)_2)_kR_{4-k}]^+$, with $0 \leq k \leq 4$, or $[C(N(R^7)_2)_3]^+$, wherein each of the substituents $R^7$ are the same or different, representing

H, $C_oF_{2o+1-p-q}H_pA_q$, or

A, wherein $1 \leq o \leq 10$, $0p \leq 2o+1$, $0 \leq q \leq 2o+1$, preferably $1 \leq o \leq 6$, $0 \leq p \leq 2o+1$, and $0 \leq q \leq 2o+1$, and A represents an aromatic residue optionally having heteroatoms, or a preferably 5- or 6-membered cycloalkyl residue.

All of the aromatic, heteroaromatic or cycloaliphatic compounds well-known to those skilled in the art and suitable in the preparation of $[N(R^7)_4]^+$, $[P(N(R^7)_2)_kR_{4-k}]^+$, with $0 \leq k \leq 4$, or $[C(N(R^7)_2)_3]^+$ cations can be used as aromatic or cycloaliphatic residue A optionally including heteroatoms.

Preferably, A represents a 5- or 6-membered aromatic or cycloaliphatic residue optionally including nitrogen and/or sulfur and/or oxygen atoms, more preferably a phenyl or pyridine residue.

In another preferred embodiment of the present invention, the cation $M^{n+}$ is a heteroaromatic cation selected from the group of heteroaromatic cations of general formulas (II) to (IX):

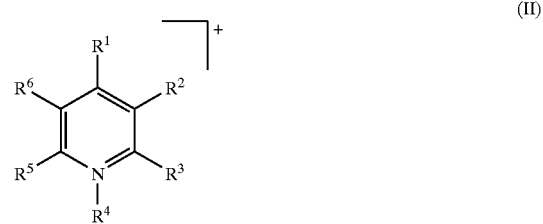

(II)

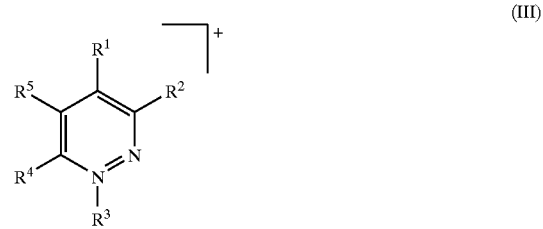

(III)

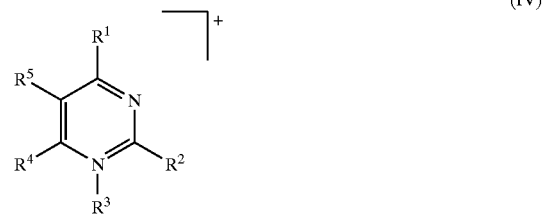

(IV)

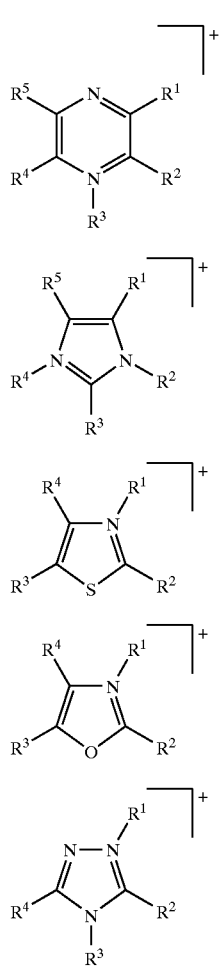

(V)

(VI)

(VII)

(VIII)

(IX)

The residues $R^1$ to $R^6$, each of which may be the same or different, represent H, a halogen, preferably fluorine, or a $C_{1-8}$ alkyl residue optionally substituted by F, Cl, $N(C_aF_{(2a+1-b)}H_b)_2$, $O(C_aF_{(2a+1-b)}H_b)$, $SO_2(C_aF_{(2a+1-b)}H_b)$, or $C_aF_{(2a+1-b)}H_b$ substituents wherein $1 \leq a \leq 6$, and $0 \leq b \leq 2a+1$.

Likewise, two of the residues $R^1$ to $R^6$ together may represent a $C_{1-8}$ alkyl residue optionally substituted by F, Cl, $N(C_aF_{(2a+1-b)}H_b)_2$, $O(C_aF_{(2a+1-b)}H_b)$, $SO_2(C_aF_{(2a+1-b)}H_b)$, or $C_aF_{(2a+1-b)}H_b$ substituents wherein $1 \leq a \leq 6$, and $0 \leq b \leq 2a+1$.

Also preferred are tetrakisfluoroalkylborate salts of general formula (I) wherein each of the ligands R are the same, representing $(C_xF_{2x+1})$, and x=1 or 2. Those tetrakisfluoroalkylborate salts are particularly preferred wherein each of the ligands R are the same, representing a $CF_3$ residue.

The salts of the invention having the general formula (I) can be used both in pure form and in the form of mixtures thereof as conducting salts in electrolytes, primary and secondary batteries, capacitors, supercapacitors and/or galvanic cells. As conducting salts, it is also possible to use the salts according to the invention in mixture with other lithium salts well-known to those skilled in the art.

They can be used in amounts of between 1 and 99% in combination with other conducting salts that find use in electrochemical cells. For example, conducting salts selected from the group of $LiPF_6$, $LiBF_4$, $LiClO_4$, $LiAsF_6$, $LiCF_3SO_3$, $LiN(CF_3SO_2)_2$, $LiC(CF_3SO_2)_3$ and mixtures of at least two of these compounds are suitable.

The salts of formula (I) and mixtures thereof can also be used in electrolytes for electrochemical cells.

The electrolytes may also include organic isocyanates (DE 100 42 149) to reduce the water content.

Compounds of general formula $$[([R^1(CR^2R^3)_k]_lA_x)_yKt]^+(CF_3)_2N^-$$

wherein

Kt represents N, P, As, Sb, S, Se,

A represents N, P, P(O), O, S, S(O), $SO_2$, As, As(O), Sb, Sb(O), $R^1$, $R^2$ and $R^3$, same or different, represent H, halogen, substituted and/or unsubstituted alkyl $C_nH_{2n+1}$, substituted and/or unsubstituted alkenyl having 1–18 carbon atoms and one or more double bonds, substituted and/or unsubstituted alkynyl having 1–18 carbon atoms and one or more triple bonds, substituted and/or unsubstituted cycloalkyl $C_mH_{2m-1}$, mono- or polysubstituted and/or unsubstituted phenyl, substituted and/or unsubstituted heteroaryl, A may be included at different positions in $R^1$, $R^2$ and/or $R^3$, Kt may be included in cyclic or heterocyclic rings; the groups bound to Kt may be the same or different, with

| | |
|---|---|
| n | 1–18, |
| m | 3–7, |
| k | 0, 1–6, |
| l | 0 or 2 if x = 1, and 1 if x = 0, |
| x | 0, 1, |
| y | 1–4, | may also be included (DE 99 41 566). The method of preparing these compounds is characterized in that an alkali salt of general formula $$D^+(CF_3)_2N^-$$

with $D^+$ selected from the group of alkali metals, is reacted in a polar organic solvent with a salt of general formula $$[([R^1(CR^2R^3)_k]_lA_x)_yKt]^+E^-$$

wherein

Kt, A, $R^1$, $R^2$, $R^3$, k, l, x, and y have the above-stated meanings, and $E^-$ represents $F^-$, $Cl^-$, $Br^-$, $I^-$, $BF_4^-$, $ClO_4^-$, $AsF_6^-$, $SbF_6^-$, or $PF_6^-$.

The mixtures according to the invention may also be included in electrolytes comprising compounds of formula $$X—(CYZ)_m—SO_2N(CR^1R^2R^3)_2,$$

with

X H,F,Cl,$C_nF_{2n+1}$, $C_nF_{2n-1}$, $(SO_2)_kN(CR^1R^2R^3)_2$,

Y H,F,Cl

Z H,F,Cl $R^1$,$R^2$,$R^3$ H and/or alkyl, fluroalkyl, cycloalkyl, m 0–9, and if X=H, m≠0, n 1–9, k 0 if m=0, and k=1–9, prepared by reacting partially fluorinated or perfluorinated alkylsulfonyl fluorides with dimethylamine in organic solvents (DE 199 53 051).

Lithium complex salts of formula

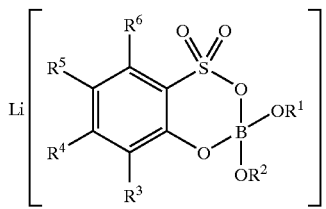

wherein $R^1$ and $R^2$ are the same or different, optionally bound directly to each other by a single or double bond, each one alone or together representing an aromatic ring from the group of phenyl, naphthyl, anthracyl or phenanthryl, which may be unsubstituted or from mono- to hexasubstituted by alkyl ($C_1$–$C_6$), alkoxy groups ($C_1$–$C_6$), or halogen (F, Cl, Br), or each one alone or together representing an aromatic heterocyclic ring from the group of pyridyl, pyrazyl or pyrimidyl, which may be unsubstituted or from mono- to tetrasubstituted by alkyl ($C_1$–$C_6$), alkoxy groups ($C_1$–$C_6$), or halogen (F, Cl, Br), or each one alone or together representing an aromatic ring from the group of hydroxybenzenecarboxyl, hydroxynaphthalenecarboxyl, hydroxybenzenesulfonyl, and hydroxynaphthalenesulfonyl, which may be unsubstituted or from mono- to tetrasubstituted by alkyl ($C_1$–$C_6$), alkoxy groups ($C_1$–$C_6$), or halogen (F, Cl, Br), $R^3$ to $R^6$, each one alone or in pairs, optionally bound directly to each other by a single or double bond, may represent the following:

1. alkyl ($C_1$–$C_6$), alkoxy ($C_1$–$C_6$), or halogen (F, Cl, Br),
2. an aromatic ring from the groups of phenyl, naphthyl, anthracyl, or phenanthryl, which may be unsubstituted or from mono- to hexasubstituted by alkyl ($C_1$–$C_6$), alkoxy groups ($C_1$–$C_6$), or halogen (F, Cl, Br), pyridyl, pyrazyl or pyrimidyl, which may be unsubstituted or from mono- to tetrasubstituted by alkyl ($C_1$–$C_6$), alkoxy groups ($C_1$–$C_6$), or halogen (F, Cl, Br), prepared using the following method (DE 199 32 317)

a) 3-, 4-, 5-, 6-substituted phenol in a suitable solvent is added with chlorosulfonic acid,
b) the intermediate from a) is reacted with chlorotrimethylsilane, filtrated and subjected to fractionated distillation,
c) the intermediate from b) is reacted with lithium borate tetramethanolate in a suitable solvent, and the final product is isolated therefrom, may also be included in the electrolyte.

Electrolytes having complex salts of general formula (DE 199 51 804)

wherein x, y represent 1, 2, 3, 4, 5, 6, $M^{x+}$ represents a metal ion,

E represents a Lewis acid selected from the group of $BR^1R^2R^3$, $AlR^1R^2R^3$, $PR^1R^2R^3R^4R^5$, $AsR^1R^2R^3R^4R^5$, $VR^1R^2R^3R^4R^5$, $R^1$ to $R^5$, same or different, optionally bound directly to each other by a single or double bond, each one alone or together may represent a halogen (F, Cl, Br), an alkyl or alkoxy residue ($C_1$–$C_8$) which may be partially or completely substituted by F, Cl, Br, an aromatic ring from the group of phenyl, naphthyl, anthracyl, or phenanthryl, optionally bound via oxygen, which may be unsubstituted or from mono- to tetrasubstituted by alkyl ($C_1$–$C_8$) or F, Cl, Br, an aromatic heterocyclic ring from the group of pyridyl, pyrazyl or pyrimidyl, optionally bound via oxygen, which may be unsubstituted or from mono- to tetrasubstituted by alkyl ($C_1$–$C_8$) or F, Cl, Br, and Z represents $OR^6$, $NR^6R^7$, $CR^6R^7R^8$, $OSO_2R^6$, $N(SO_2R^6)(SO_2R^7)$, $C(SO_2R^6)(SO_2R^7)(SO_2R^8)$, $OCOR^6$, wherein $R^6$ to $R^8$ are the same or different, optionally bound directly to each other by a single or double bond, each one alone or together representing hydrogen or having the meaning like $R^1$ to $R^5$, prepared by reacting an appropriate boron or phosphorus/Lewis acid/solvent adduct with a lithium or tetraalkylammonium imide, methanide or triflate, can also be used.

Borate salts (DE 199 59 722) of general formula

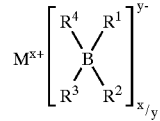

wherein

M represents a metal ion or a tetraalkylammonium ion, x, y represent 1, 2, 3, 4, 5, or 6, $R^1$ to $R^4$, same or different, represent alkoxy or carboxy residues ($C_1$–$C_8$) optionally bound directly to each other by a single or double bond, may also be included.

These borate salts are prepared by reacting lithium borate tetraalcoholate or a 1:1 mixture of lithium alcoholate and a boric acid ester in an aprotic solvent with a suitable hydroxy or carboxy compound at a ratio of 2:1 or 4:1.

Additives such as silane compounds of general formula

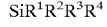

with $R^1$ to $R^4$ H, $C_yF_{2y+1-z}H_z$, $OC_yF_{2y+1-z}H_z$, $OC(O)C_yF_{2y+1-z}H_z$, $OSO_2C_yF_{2y+1-z}H_z$, and $1 \leq x \leq 6$, $1 \leq y \leq 8$, and $0 \leq z \leq 2y+1$, and $R^1$–$R^4$, same or different, representing an aromatic ring from the group of phenyl, naphthyl, which may be unsubstituted or mono- or polysubstituted by F, $C_yF_{2y+1-z}H_z$ or $OC_yF_{2y+1-z}H_z$, $OC(O)C_yF_{2y+1-z}H_z$, $OSO_2C_yF_{2y+1-z}H_z$, $N(C_nF_{2n+1-z}H_z)_2$, or representing a heterocyclic aromatic ring from the group of pyridyl, pyrazyl or pyrimidyl, each of which may be substituted by F, $C_yF_{2y+1-z}H_z$ or $OC_yF_{2y+1-z}H_z$, $OC(O)C_yF_{2y+1-z}H_z$, $OSO_2C_yF_{2y+1-z}H_z$, $N(C_nF_{2n+1-z}H_z)_2$ (DE 100 27 626), may also be included.

The compounds according to the invention can also be used in electrolytes including lithium fluoroalkylphosphates of following formula

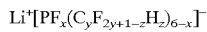

wherein $1 \leq x \leq 5$,
$3 \leq y \leq 8$,
$0 \leq z \leq 2y+1$, and the ligands $(C_yF_{2y+1-z}H_z)$ may be the same or different, with compounds of general formula $$Li^+[PF_a(CH_bF_c(CF_3)_d)_e]^-$$

wherein a is an integer of from 2 to 5, b=0 or 1, c=0 or 1, d=2, and e is an integer of from 1 to 4, with the proviso that b and c do not simultaneously represent zero, and the sum of a+e=6, and the ligands $(CH_bF_c(CF_3)_d)$ may be the same or different, being excluded (DE 100 08 955). The method of preparing lithium fluoroalkylphosphates is characterized in that at least one compound of general formula

| | |
|---|---|
| $H_mP(C_nH_{2n+1})_{3-m}$ | (III), |
| $OP(C_nH_{2n+1})_3$ | (IV), |
| $Cl_mP(C_nH_{2n+1})_{3-m}$ | (V), |
| $F_mP(C_nH_{2n+1})_{3-m}$ | (VI), |
| $Cl_oP(C_nH_{2n+1})_{5-o}$ | (VII), |
| $F_oP(C_nH_{2n+1})_{5-o}$ | (VIII), | wherein $0<m<2, 3<n<8$, and $0<o<4$, is fluorinated by electrolysis in hydrogen fluoride, the mixture of fluorination products thus obtained is separated by extraction, phase separation and/or distillation, and the fluorinated alkylphosphorane thus obtained is reacted in an aprotic solvent or mixture of solvents with lithium fluoride under exclusion of moisture, and the resulting salt is purified and isolated according to conventional methods.

The compounds according to the invention may also be used in electrolytes including salts of formula $$Li[P(OR^1)_a(OR^2)_b(OR^3)_c(OR^4)_dF_e]$$

wherein $0 \leq a+b+c+d \leq 5$, and $a+b+c+d+e=6$, and $R^1$ to $R^4$ independently are alkyl, aryl or heteroaryl residues, and at least two of $R^1$ to $R^4$ may be bound directly to each other by a single or double bond (DE 100 16 801). These compounds are prepared by reacting phosphorus(V) compounds of general formula $$P(OR^1)_a(OR^2)_b(OR^3)_c(OR^4)_dF_e$$

wherein $0 \leq a+b+c+d \leq 5$, and $a+b+c+d+e=5$, and $R^1$ to $R^4$ have the above-stated meanings, with lithium fluoride in the presence of an organic solvent.

Ionic liquids of general formula $$K^+A^-$$

wherein $K^+$ represents a cation selected from the group of

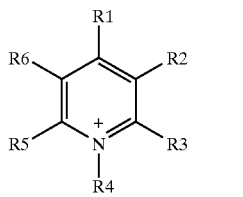
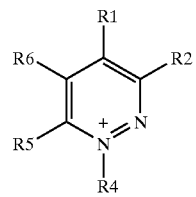
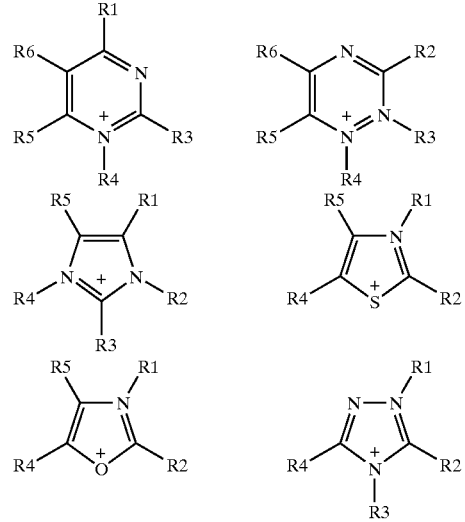

wherein $R^1$ to $R^5$ are the same or different, optionally bound directly to each other by a single or double bond, each one alone or together representing the following:

H, halogen, alkyl residue $(C_1-C_8)$ which may be partially or completely substituted by F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, with $1<n<6$, and $0<x<13$, and $A^-$ represents an anion selected from the group of $$[B(OR^1)_n(OR^2)_m(OR^3)_o(OR^4)_p]^-$$

with $0 \leq n, m, o, p \leq 4$, and
$m+n+o+p=4$, wherein $R^1$ to $R^4$ are different, or pairs thereof are the same, optionally bound directly to each other by a single or double bond, each one alone or together representing an aromatic ring from the group of phenyl, naphthyl, anthracyl, or phenanthryl, which may be unsubstituted or mono- or polysubstituted by $C_nF_{(2n+1-x)}H_x$, with $1<n<6$, and $0<x \leq 13$, or halogen (F, Cl, Br), or representing an aromatic heterocyclic ring from the group of pyridyl, pyrazyl or pyrimidyl, which may be unsubstituted or mono- or polysubstituted by $C_nF_{(2n+1-x)}H_x$, with $1<n<6$, and $0<x \leq 13$, or halogen (F, Cl, Br), or representing an alkyl residue $(C_1-C_8)$ which may be partially or completely substituted by additional groups, preferably F, Cl, $N(C_nF_{(2n+1-x)}H_x)_2$, $O(C_nF_{2n+1-x}H_x)$, $SO_2(C_nF_{(2n+1-x)}H_x)$, $C_nF_{(2n+1-x)}H_x$, with $1<n \leq 6$, and $0<x \leq 13$, or wherein $OR^1$ to $OR^4$, each one alone or together, represent an aromatic or aliphatic carboxyl, dicarboxyl, oxysulfonyl, or oxycarboxyl residue which may be partially or completely substituted by additional groups preferably F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, with $1<n<6$, and $0<x \leq 13$ (DE 100 26 565), may be included in the electrolyte.

Ionic liquids $K^+A^-$ wherein $K^+$ is as defined above and A represents an anion selected from the group of $$[PF_x(C_yF_{2y+1-z}H_z)_{6-x}]^-$$

with
$1 \leq x \leq 6$,
$1 \leq y \leq 8$, and
$0 \leq z \leq 2y+1$,
may also be included (DE 100 27 995).

The compounds according to the invention can be used in electrolytes for electrochemical cells including an anode material which consists of coated metal cores selected from the group of Sb, Bi, Cd, In, Pb, Ga, and tin, or alloys thereof (DE 100 16 024). The process for producing such anode material is characterized in that
  a) a suspension or sol of the core metal or alloy in urotropine is prepared,
  b) the suspension is emulsified with $C_5$–$C_{12}$ hydrocarbons,
  c) the emulsion is precipitated on the metal or alloy core, and
  d) the metal hydroxides or oxyhydroxides are converted to the corresponding oxides by tempering.

The compounds according to the invention can also be used in electrolytes for electrochemical cells with cathodes made of common lithium intercalation and insertion compounds, but also with cathode materials consisting of lithium mixed oxide particles which are coated with one or more metal oxides (DE 199 22 522) by suspending the particles in an organic solvent, adding to the suspension a solution of a hydrolyzable metal compound and a hydrolyzing solution, and subsequently filtrating, drying and optionally calcining the coated particles. Said materials may also consist of lithium mixed oxide particles coated with one or more polymers (DE 199 46 066), obtained using a process wherein the particles are suspended in a solvent, and the coated particles subsequently are filtrated off, dried and optionally calcined. Likewise, the compounds according to the invention can be used in systems including cathodes comprised of lithium mixed oxide particles having one or more coatings of alkali metal compounds and metal oxides (DE 100 14 884). The process for producing these materials is characterized in that the particles are suspended in an organic solvent, an alkali metal salt compound suspended in an organic solvent is added, metal oxides dissolved in an organic solvent are added, the suspension is added with a hydrolyzing solution, and the coated particles subsequently are filtrated off, dried and calcined. Likewise, the compounds according to the invention can be used in systems including anode materials with doped tin oxide (DE 100 25 761). Such an anode material is prepared by
  a) adding urea to a tin chloride solution,
  b) adding the solution with urotropine and a suitable doping compound,
  c) emulsifying the sol thus obtained in petroleum ether,
  d) washing the resulting gel, and removing the solvent by suction, and
  e) drying and tempering the gel.

Likewise, the compounds according to the invention can be used in systems including anode materials with reduced tin oxide (DE 100 25 762). This anode material is produced by
  a) adding urea to a tin chloride solution,
  b) adding the solution with urotropine,
  c) emulsifying the sol thus obtained in petroleum ether,
  d) washing the resulting gel, and removing the solvent by suction,
  e) drying and tempering the gel, and
  f) exposing the resulting $SnO_2$ to a stream of reducing gas in a gas-feedable oven.

Preferably, the salts according to the invention are used as conducting salts in their pure form, because particularly good reproducibility of the electrochemical properties can be ensured in this way.

The invention is also directed to a method of producing the tetrakisfluoroalkylborate salts of the invention having the general formula (I) wherein the ligands R each are identical, representing a $CF_3$ residue.

In this method, at least one salt of general formula (X)

$$M^{n+}([B(CN)_4]^-)_n \qquad (X)$$

wherein $M^{n+}$ and n have the above-stated meanings, is fluorinated by reacting with at least one fluorinating agent in at least one solvent, and the fluorinated compound of general formula (I) thus obtained is purified and isolated according to methods well-known to those skilled in the art.

Immediately subsequent to fluorination, the tetrakisfluoroalkylborate salts frequently have a purity of >99%. If necessary, further purification of the salts can be effected according to methods well-known to those skilled in the art, e.g. by recrystallization in a suitable solvent or mixture of solvents. A person skilled in the art may select suitable solvents or mixtures of solvents by means of simple preliminary tests.

The compounds of general formula (X) can be synthesized in analogy to the method published in E. Bernhardt, G. Henkel, H. Willner, Z. Anorg. Allg. Chem. 2000, Vol. 626, p. 560. This citation is hereby incorporated by reference and is deemed to be part of the disclosure.

In the method according to the invention, the reaction with the fluorinating agent preferably is effected at a temperature ranging from –80 to +20° C., more preferably at a temperature ranging from –60 to 0° C.

In the method according to the invention, it is preferred to use fluorine, chlorine fluoride, chlorine trifluoride, chlorine pentafluoride, bromine trifluoride, bromine pentafluoride, or a mixture of at least two of these fluorinating agents as suitable fluorinating agents. The use of chlorine fluoride, chlorine trifluoride or a mixture of at least two fluorinating agents containing chlorine fluoride and/or chlorine trifluoride is particularly preferred.

It is preferred to use hydrogen fluoride, iodine pentafluoride, dichloromethane, chloroform, or a mixture of at least two of these solvents as suitable solvent in the fluorination of the salts of general formula (X). It is particularly preferred to use hydrogen fluoride as solvent.

The tetrakisfluoroalkylborate salts of general formula (I) are also suitable for use in solid electrolytes. In the meaning of the invention, solid electrolytes are understood to be polymer electrolytes normally having an optionally crosslinked polymer and a conducting salt, as well as gel electrolytes which, in addition to an optionally crosslinked polymer and a conducting salt, include at least one solvent.

The present invention therefore is also directed to a mixture including
  a) at least one tetrakisfluoroalkylborate salt of general formula (I), and
  b) at least one polymer.

Mixtures in the meaning of the present invention include pure mixtures of components a) and b), mixtures wherein the salt of component a) is included in the polymer of component b), and mixtures wherein chemical and/or physical bonds exist between the salt of component a) and the polymer of component b).

In a preferred embodiment of the present invention, the mixture of the invention includes from 5 to 99 wt.-% of component a) and from 95 to 1 wt.-% of component b), more preferably from 60 to 99 wt.-% of component a) and from 40 to 1 wt.-% of component b). Each of the specified weight ratios relates to the sum of components a) and b).

As component b), the mixture according to the invention preferably includes a homopolymer or copolymer of unsaturated nitriles, preferably acrylonitrile, vinylidenes, preferably vinylidene difluoride, acrylates, preferably methyl acrylate, methacrylates, preferably methyl methacrylate, cyclic ethers, preferably tetrahydrofuran, alkylene oxides, preferably ethylene oxide, siloxane; phosphazene, alkoxysilanes, or an organically modified ceramic, or a mixture of at least two of the above-mentioned homopolymers and/or-copolymers and optionally at least one organically modified ceramic.

Preferably, inorganic-organic hybrid polymers are possible as organically modified ceramics, which polymers are obtained by hydrolysis and fusion of organically modified silicon alkoxides and subsequent crosslinking of the crosslinkable groups fixed on the inorganic backbone. For example, appropriate organically modified ceramics are being marketed under the name of ORMOCERE®.

More preferably, component b) is a homopolymer or copolymer of vinylidene difluoride, acrylonitrile, methyl (meth)acrylate, tetrahydrofuran, and especially preferably a homopolymer or copolymer of vinylidene difluoride.

These homo- and copolymers of vinylidene difluoride are being marketed under the names of Kynar® and Kynarflex® by Atofina Chemicals; Inc., and under the name of Solef® by the Solvay Company.

The polymers used according to the invention may also be at least partially crosslinked. Crosslinking can be effected according to conventional methods well-known to those skilled in the art, using well-known crosslinking agents. Crosslinking may also be effected in the presence of component a) and optionally additional components.

In addition to the tetrakisfluoroalkylborate salts of general formula (I) and the polymers, the mixture according to the invention may include a solvent or a mixture of solvents comprised of two or more solvents.

Preferred solvents are organic carbonates, preferably ethylene carbonate, propylene carbonate, butylene carbonate, dimethyl carbonate, diethyl carbonate, ethyl methyl carbonate, or methyl propyl carbonate, organic esters, preferably methyl formate, ethyl formate, methyl acetate, ethyl acetate, methyl propionate, ethyl propionate, methyl butyrate, ethyl butyrate, γ-butyrolactone, organic ethers, preferably diethyl ether, dimethoxyethane, diethoxyethane, organic amides, preferably dimethylformamide or dimethylacetamide, sulfur-containing solvents, preferably dimethylsulfoxide, dimethyl sulfite, diethyl sulfite, or propanesultone, aprotic solvents, preferably acetonitrile, acrylonitrile, or acetone, or at least partially fluorinated derivatives of the above-mentioned solvents, or mixtures of at least two of these solvents and/or fluorinated derivatives of these solvents.

The present invention also is directed to a method of producing the mixtures of the invention, according to which at least one of the above-mentioned tetrakisfluoroalkylborate salts of general formula (I) and at least one polymer and optionally at least one solvent are mixed together.

Preferably, the above components are mixed at elevated temperature, more preferably at 20 to 90° C., with 40 to 60° C. being particularly preferred, and these temperatures may vary depending on the components employed.

The present invention is also directed to the use of at least one tetrakisfluoroalkylborate salt according to the invention or of a mixture according to the invention in electrolytes, primary batteries, secondary batteries, capacitors, supercapacitors, and/or galvanic cells, optionally in combination with other well-known conducting salts and/or additives.

Furthermore, the tetrakisfluoroalkylborate salts according to the invention are suitable in the polymerization of olefins. They are also suitable in the production of catalytically active compounds wherein the tetrakisfluoroalkylborate anions function as counterions of the cationic catalysts. Therefore, the present invention is also directed to the use of the tetrakisfluoroalkylborate salts in the polymerization of olefins and in the production of catalysts.

The invention is also directed to electrolytes, primary and secondary batteries, capacitors, supercapacitors, and galvanic cells including at least one tetrakisfluoroalkylborate salt according to the invention having general formula (I) or a mixture according to the invention and optionally other conducting salts and/or additives. Other conducting salts and additives are known to those skilled in the art, e.g. from Doron Auerbach, Nonaqueous Electrochemistry, Marc Dekker Inc., New York, 1999; D. Linden, Handbook of Batteries, Second Edition, McGraw-Hill Inc., New York, 1995; as well as G. Mamantov and A. I. Popov, Chemistry of Nonaqueous Solutions, Current Progress, VCH Verlagsgesellschaft, Weinheim, 1994. These citations are hereby incorporated by reference and are deemed to be part of the disclosure.

The electrolytes according to the invention preferably include concentrations of the tetrakisfluoroalkylborate salts of the invention of from 0.01 to 3 mol/l, more preferably from 0.01 to 2 mol/l, with 0.1 to 1.5 mol/l being particularly preferred.

As solvents for the salts of the invention, the electrolyte preferably include organic carbonates, preferably ethylene carbonate, propylene carbonate, butylene carbonate, dimethyl carbonate, diethyl carbonate, ethyl methyl carbonate, or methyl propyl carbonate, organic esters, preferably methyl formate, ethyl formate, methyl acetate, ethyl acetate, methyl propionate, ethyl propionate, methyl butyrate, ethyl butyrate, γ-butyrolactone, organic ethers, preferably diethyl ether, dimethoxyethane, diethoxyethane, organic amides, preferably dimethylformamide or dimethylacetamide, sulfur-containing solvents, preferably dimethylsulfoxide, dimethyl sulfite, diethyl sulfite, or propanesultone, aprotic solvents, preferably acetonitrile, acrylonitrile, or acetone, or at least partially fluorinated derivatives of the above-mentioned solvents, or mixtures of at least two of these solvents and/or fluorinated derivatives of these solvents.

The tetrakisfluoroalkylborate salts according to the invention and the mixtures of the invention are advantageous in that signs of decomposition in the presence of water are absent or nearly absent over a long period of time, and that they have from good to very good solubility in most solvents or mixtures of solvents.

Furthermore, they have high thermal stability and high chemical stability both in the solid and dissolved states. Thus, the salts and mixtures according to the invention are stable with respect to strong oxidants such as fluorine.

By virtue of these properties, electrolytes, batteries, capacitors, supercapacitors, and galvanic cells including these conducting salts can also be used under extreme conditions, such as high temperatures, with no adverse effects on their service life and performance by such conditions.

Furthermore, these batteries, capacitors, supercapacitors, and galvanic cells are remarkable for their highly constant voltage, unrestricted functionality over many charge/discharge cycles, as well as low production cost.

The use of the tetrakisfluoroalkylborate slats or mixtures according to the invention in large batteries, such as those used in electric road vehicles or hybrid road vehicles is also highly advantageous, because no toxic and strongly etching hydrogen fluoride will be formed upon damage of the batteries, e.g. in case of an accident, not even upon contact with water, e.g. humidity or fire-fighting water.

With reference to the examples, the invention will be illustrated below. These examples merely are intended to illustrate the invention and do not limit the general idea of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure[s] of all applications, patents, and publications, cited above [or below], and of corresponding German Application No. 10055811.9, filed Nov. 10, 2000 is hereby incorporated by reference.

EXAMPLES

Example 1

Synthesis of potassium tetrakistrifluorometylborate, $K[B(CF_3)_4]$

1a)

85 mg (0.60 mmol) of NH4[B(CN)4] was dried under vacuum in a 250 ml PFA (tetrafluoroethylene/perfluorinated propyl vinyl ether copolymer) reactor. Subsequently, about 5 ml of hydrogen fluoride and 28.4 mmol of chlorine fluoride (metered by gas-volumetric means) were condensed into the reactor. The reaction mixture was slowly heated at a temperature of from 20 to 25° C. with stirring, and stirring was continued for another 48 hours at this temperature. Thereafter, all of the volatile components were removed from the reaction mixture under vacuum. The residue thus obtained was taken up in about 5 ml of distilled water, neutralized with 200 mg of potassium carbonate, and the water then was removed under vacuum. The potassium tetrakistrifluoromethylborate, $K[B(CF_3)_4]$, was extracted with diethyl ether from the resulting residue. The diethyl ether was distilled off to yield 173 mg (0.53 mmol) of $K[B(CF_3)_4]$.

Alternatively, the synthesis of $K[B(CF_3)_4]$ can be performed according to the protocols 1b) or 1c):

1b)

1.512 g (11.4 mmol) of $NH_4[B(CN)_4]$ was dried under vacuum in a 500 ml stainless steel autoclave. Subsequently, about 30–40 ml of hydrogen fluoride and 562 mmol of chlorine fluoride (metered by gas-volumetric means) were condensed into the reactor. The reaction mixture then was slowly heated at a temperature of from 20 to 25° C. with stirring, and stirring was continued for another 48–72 hours at this temperature. Thereafter, all of the volatile components were removed from the reaction mixture under vacuum. The residue thus obtained was taken up in about 50 ml of distilled water, neutralized with 3.8 g of potassium carbonate, and the water then was removed under vacuum. The potassium tetrakistrifluoromethylborate, $K[B(CF_3)_4]$, was extracted with diethyl ether from the resulting residue. The diethyl ether was distilled off to yield 3.4 g (11.2 mmol) of $K[B(CF_3)_4]$.

1c)

105 mg (0.79 mmol) of $NH_4[B(CN)_4]$ was dried under vacuum in a 250 ml PFA(tetrafluoroethylene/perfluorinated propyl vinyl ether copolymer) reactor. Subsequently, about 5 ml of hydrogen fluoride and 11.4 mmol of chlorine trifluoride (metered by gas-volumetric means) were condensed into the reactor. The reaction mixture then was slowly heated at a temperature of from 20 to 25° C. with stirring, and stirring was continued for another 19 hours at this temperature. Thereafter, all of the volatile components were removed from the reaction mixture under vacuum. The residue thus obtained was taken up in about 7 ml of distilled water, neutralized with 300 mg of potassium carbonate, and the water then was removed under vacuum. The potassium tetrakistrifluoromethylborate, $K[B(CF_3)_4]$, was extracted with diethyl ether from the resulting residue. The diethyl ether was distilled off to yield 209 mg (0.69 mmol) of $K[B(CF_3)_4]$.

Part of the $K[B(CF_3)_4]$ was dissolved in deuterated acetonitrile (200 mg/ml, 1 mol/25 mol $CD_3CN$) and characterized using $^{11}B$ and $^{19}F$ NMR spectroscopy. The $^{11}B$ NMR spectrum was recorded at a frequency of 160.5 MHz, the $^{19}F$ NMR spectrum at 470.6 MHz, and the $^{13}C$ NMR spectrum at 125.8 MHz. As internal standard, $(C_2H_55)_2OBF_3$ with $\delta=0$ ppm was used in the $^{11}B$ NMR spectroscopy, $CFCl_3$ with $\delta=0$ ppm in the $^{19}F$ NMR spectroscopy, and tetramethylsilane (TMS) with $\delta=0$ ppm in the $^{13}C$ NMR spectroscopy. The NMR-spectroscopic data were as follows:

$^{11}B$ NMR spectrum: $\delta=-18.94$ ppm, $^2J(^{11}B^{19}F)=25.92$ Hz, $^1J(^{11}B^{13}C)=73.4$ Hz, $^1\Delta^{11}B(^{12/13}C)=0.0030$ ppm at a line width of 0.5 Hz.

$^{19}F$ NMR spectrum: $\delta=-61.60$ ppm, $^2J(^{19}F^{11}B)=25.92$ Hz, $^2J(^{19}F^{10}B)=8.68$ Hz, $^2\Delta^{19}F(^{10/11}B)=0.0111$ ppm, $^1J(^{19}F^{13}C)=304.3$ Hz, $^1\Delta^{19}F(^{12/13}C)=0.1315$ ppm, $^3J(^{19}F^{13}C)=3.9$ Hz, $^3\Delta^{19}F(^{12/13}C)=0.0010$ ppm, $^4J(^{19}F^{19}F)=5.8$ Hz at a line width of 0.4 Hz.

$^{13}C$ NMR spectrum: $\delta=132.9$ ppm, $^1J(^{13}C^{19}F)=304.3$ Hz, $^3J(^{13}C^{19}F)=4.0$ Hz, $^1J(^{13}C^{11}B)=73.4$ Hz, $^1J(^{13}C^{10}B)=24.6$ Hz, $^1\Delta^{13}C(^{10/11}B)=0.0029$ ppm at a line width of 1.5 Hz.

The purity of the potassium tetrakistrifluoromethylborate thus obtained was >99%. $K[B(CF_3)_4]$ is readily soluble in water, diethyl ether and acetonitrile, but insoluble in dichloromethane, pentane and heptane. According to the differential scanning calorimetry measurements, the salt is stable in the solid state up to 320° C. ($\Delta H=-90$ J/g), having two phase transformations at $-63°$ C. ($\Delta H=4.5$ J/g) and $-47°$ C. ($\Delta H=7.8$ J/g).

When using other carbonates or mixtures thereof instead of potassium carbonate in the neutralization of the respective crude product, e.g. lithium carbonate, sodium carbonate, rubidium carbonate, or cesium carbonate, the corresponding lithium, sodium, rubidium, or cesium tetrakistrifluoromethylborate salts can be obtained in an analogous fashion, the corresponding lithium or sodium salt having solvent molecules bound therein which can be removed successively by slowly heating the respective salt.

Example 2

Synthesis of $[Li(THF)_x][B(CF_3)_4]$ 173 mg of $K[B(CF_3)_4]$ (0.57 mmol) and 24 mg of lithium chloride were dried under vacuum in a 50 ml glass flask equipped with a polytetrafluoroethylene valve. Subsequently, about 10 ml of tetrahydrofuran was condensed into the flask, and the reaction mixture was stirred for one hour at a temperature of from 20 to 25° C. A precipitate of potassium chloride formed which subsequently was filtrated off. The solution thus obtained was thoroughly concentrated at a temperature of from 20 to 25° C. under vacuum. Following removal of the tetrahydrofuran, 300 mg of [Li(THF)$_x$][B(CF$_3$)$_4$] was obtained.

In its solid state, lithium tetrakistrifluoromethylborate is stable up to 168° C. (ΔH=−260 J/g). It is readily soluble in water, tetrahydrofuran, acetonitrile, methanol, and acetone. The tetrahydrofuran solvate molecules are removed one by one up to 140° C. (97° C., ΔH=7 g/J, 130° C., ΔH=4 J/g).

Example 3

Synthesis of Li[B(CF$_3$)$_4$]

4.233 g (12.99 mmol) of K[B(CF$_3$)$_4$] and 1.225 g (13.07 mmol) of LiBF$_4$ were added to 13.052 g of a solvent mixture of ethylene carbonate, dimethyl carbonate and diethyl carbonate at a ratio of 2:1:2. A precipitate of KBF$_4$ formed which was removed by filtration. The solution of Li[B(CF$_3$)$_4$] (14.522 g, 11.7 ml) thus obtained had a salt concentration of 22.6wt.-% or 0.96 mol/l.

Example 4

Synthesis of 1-ethyl-3-methylimidazolium tetrakistrifluoromethylborate

Equimolar amounts of potassium tetrakistrifluoromethylborate and 1 ethyl-3-methylimidazolium chloride were suspended in acetonitrile at a temperature of from 20 to 25° C. Subsequently, this mixture was stirred for 10 hours at this temperature and vacuum-filtrated over a glass frit with cooling so as to completely remove the potassium chloride having formed. The solvent was distilled off under vacuum, and the product thus obtained was dried under vacuum.

Example 5

Comparison of the ionic conductance of Li[B(CF$_3$)$_4$] and LiPF$_5$

Solutions of each salt in a mixture of ethylene carbonate, diethyl carbonate and dimethyl carbonate at a volume ratio of 2:1:2 were prepared and measured at a temperature of 25° C.

The conductivity measurements were carried out using a Knick 703 conductometer and a Knick 4-pole measuring cell with jacket tube. Thermostatting was effected in a TI 4 conditioning cabinet, and the temperature was controlled using a Pt 100 resistance thermometer.

The respective concentrations and the respective ionic conductivities are illustrated in Table 1 below:

TABLE 1

|  | Li[B(CF$_3$)$_4$] | LiPF$_6$ |
| --- | --- | --- |
| Concentration of solution [mol/I] | 0.96 | 1 |
| Ionic conductivity [mS/cm] | 10.1 | 9.6 |

Compared to LiPF$_6$, the Li[B(CF$_3$)$_4$] salt according to the invention has an improved ionic conductance.

Example 6

Tests relating to the electrochemical stability of Li[B(CF$_3$)$_4$]

In a measuring cell including platinum working electrode, lithium counterelectrode and lithium reference electrode, three consecutive cyclovoltammograms were recorded on a 0.96 molar solution of Li[B(CF$_3$)$_4$] in ethylene carbonate, diethyl carbonate and dimethyl carbonate (volume ratio 2:1:2). To this end, starting from the rest potential, the potential initially was increased to 6.0 V against the potential of Li/Li$^+$ at an advance rate of 10 mV/s and then lowered to return to the rest potential. The cyclovoltammograms thus obtained indicated no evidence of electrolyte decomposition.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A tetrakisfluoroalkylborate salt of general formula (I)

wherein

M$^{n+}$ is a univalent, bivalent, or trivalent cation, each of the ligands R are the same and straight-chained or branched, representing (C$_x$F$_{2x+1}$), with 1≦x≦8, and n=1, 2 or 3.

2. A tetrakisfluoroalkylborate salt according to claim 1, wherein the M$^{n+}$ cation is an alkali metal cation.

3. A tetrakisfluoroalkylborate salt according to claim 1, wherein the M$^{n+}$ cation is a magnesium or aluminum cation.

4. A tetrakisfluoroalkylborate salt according to claim 1, wherein M$^{n+}$ is an organic cation.

5. A tetrakisfluoroalkylborate salt according to claim 4, wherein 1≦o≦6, 0≦p≦2o+1, and 0≦q≦2o+1, and A represents an aromatic residue optionally having heteroatoms, or a 5- or 6-membered cycloalkyl residue.

6. A tetrakisfluoroalkylborate salt according to claim 4, wherein A represents a 5- or 6-membered aromatic residue optionally including nitrogen and/or sulfur and/or oxygen atoms, or a 5- or 6-membered cycloalkyl residue.

7. A tetrakisfluoroalkylborate salt according to claim 4, wherein A is a phenyl or pyridine residue.

8. A tetrakisfluoroalkylborate salt according to claim 1, wherein M$^{n+}$ is a heteroaromatic cation of general formulas (II) to (IX):

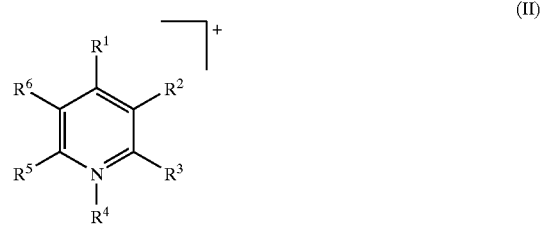

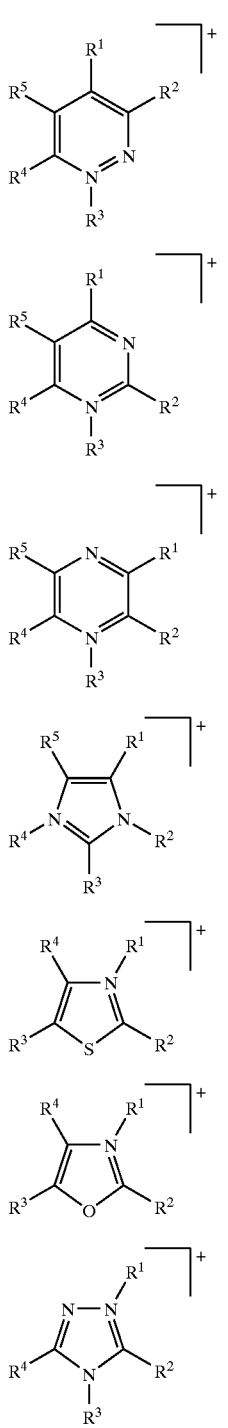

wherein
the residues $R^1$ to $R^6$, each of which is the same or different, and optionally two of the residues $R^1$ to $R^6$ together, represent H, a halogen, or a $C_{1-8}$ alkyl residue optionally substituted by F, Cl, $N(C_aF_{(2a+1-b)}H_b)_2$, $O(C_aF_{(2a+1-b)}H_b)$, $SO_2(C_aF_{(2a+1-b)}H_b)$, or $C_aF_{(2a+1-b)}H_b$, wherein $1 \leq a \leq 6$, and $0 \leq b \leq 2a+1$.

9. A tetrakisfluoroalkylborate salt according to claim 8, wherein the halogen is fluorine.

10. A tetrakisfluoroalkylborate salt according to claim 1, wherein the ligands R are the same, representing $(C_xF_{2x+1})$, with $x=1$ or 2.

11. A tetrakisfluoroalkylborate salt according to claim 1, wherein each of the ligands R are the same, representing a $CF_3$ residue.

12. A tetrakisfluoroalkylborate salt according to claim 1, wherein the $M^{n+}$ cation is a lithium, sodium or potassium cation.

13. A tetrakisfluoroalkylborate salt according to claim 1, wherein the $M^{n+}$ cation is a lithium cation.

14. A tetrakisfluoroalkylborate salt according to claim 1, wherein the $M^{n+}$ cation is a nitrosyl cation, a nitryl cation, or an organic cation of general formula $[N(R^7)_4]^+$, $[P(N(R^7)_2)_kR_{4-k}]^+$, with $0 \leq k \leq 4$, or $[C(N(R^7)_2)_3]^+$, wherein each of the residues $R^7$ are the same or different, representing
H,
$C_oF_{2o+1-p-q}H_pA_q$, or
A,
wherein
$1 \leq o \leq 10$,
$0 \leq p \leq 2o+1$,
$0 \leq q \leq 2o+1$, and
A represents an aromatic residue optionally having heteroatoms, or a 5- or 6-membered cycloalkyl residue.

15. A method of producing a tetrakisfluoroalkylborate salt of claim 11, wherein at least one compound of general formula (X)

$$M^{n+}([B(CN)_4]^-)_n \qquad (X)$$

is fluorinated by reacting with at least one fluorinating agent in at least one solvent, and the thus-obtained fluorinated compound having the general formula (I) is purified and isolated.

16. A method according to claim 15, wherein the reaction with the fluorinating agent is performed at a temperature ranging from −80 to +20° C.

17. A method according to claim 15, wherein fluorine, chlorine fluoride, chlorine trifluoride, chlorine pentafluoride, bromine trifluoride, bromine pentafluoride, or a mixture of at least two of these fluorinating agents is used as a fluorinating agent.

18. A method according to claim 15, wherein hydrogen fluoride, iodine pentafluoride, dichloromethane, chloroform, or a mixture of at least two of these substances is used as a solvent.

19. A method according to claim 15, wherein the reaction with the fluorinating agent is performed at −60–0° C.

20. A method according to claim 15, wherein chlorine fluoride, chlorine trifluoride, or a mixture of at least two fluorinating agents comprising chlorine fluoride and/or chlorine trifluoride is used as a fluorinating agent.

21. A method according to claim 15, wherein hydrogen fluoride is used as a solvent.

22. A mixture, comprising:
a) at least one tetrakisfluoroalkylborate salt of general formula (I) according to claim 1, and
b) at least one polymer.

23. A mixture according to claim 22, wherein the mixture comprises 5–99 wt.-% of component a) and 95–1 wt.-% of component b).

24. A mixture according to claim 22, wherein a component b) is a homopolymer or copolymer of an unsaturated nitrile, a vinylidene, an acrylate, a methacrylate, a cyclic ether, an alkylene oxide, a siloxane, a phosphazene, an alkoxysilane, or an organically modified ceramic, or a mixture of at least two of the above-mentioned homopolymers and/or copolymers and optionally at least one organically modified ceramic.

25. A mixture according to claim 24, wherein the component b) is a homopolymer or copolymer of vinylidene difluoride, acrylonitrile, methyl(meth)acrylate, or tetrahydrofuran.

26. A mixture according to claim 24, wherein the unsaturated nitrile is acrylonitrile, the vinylidene is a vinylidene difluoride, the acrylate is a methyl acrylate, the methacrylate is a methyl methacrylate, the cyclic ether is a tetrahydrofuran, or the alkylene oxide is an ethylene oxide.

27. A mixture according to claim 24, wherein the component b) is a homopolymer or copolymer of vinylidene difluoride.

28. A mixture according to claim 22, wherein the polymer is at least partially crosslinked.

29. A mixture according to claim 22, wherein the mixture further comprises at least one solvent.

30. A mixture according to claim 29, wherein a solvent is an organic carbonate, an organic ester, an organic ether, an organic amide, a sulfur-containing solvent, an aprotic solvent, or at least a partially fluorinated derivative of the above-mentioned compounds, or a mixture of at least two of these compounds and/or fluorinated derivatives.

31. A mixture according to claim 20, wherein the organic carbonate is ethylene carbonate, propylene carbonate, butylene carbonate, dimethyl carbonate, diethyl carbonate, ethyl methyl carbonate, or methyl propyl carbonate; the organic ester is methyl formate, ethyl formate, methyl acetate, ethyl acetate, methyl propionate, ethyl propionate, methyl butyrate, ethyl butyrate, or γ-butyrolactone; the organic ether is diethyl ether, dimethoxyethane, or diethoxyethane; the organic amide is dimethylformamide or dimethylacetamide; the sulfur-containing solvent is dimethylsulfoxide, dimethyl sulfite, diethyl sulfite, or propanesultone; or the aprotic solvent is acetonitrile, acrylonitrile, or acetone.

32. A mixture according to claim 22, wherein the mixture comprises 60–99 wt.-% of component a) and from 40–1 wt.-% of component b).

33. A method of producing a mixture according to claim 22, wherein at least one tetrakisfluoroalkylborate salt of general formula (I)

$$M^{n+}([BR_4]^-)_n \quad (I)$$

wherein

M$^{n+}$ is a univalent, bivalent, or trivalent cation, each of the ligands R are the same and straight-chained or branched, representing $(C_xF_{2x+1})$ with $1 \leq x \leq 8$, and n=1, 2 or 3, and at least one polymer and optionally at least one solvent are mixed.

34. A method according to claim 33, wherein said mixing is effected at an elevated temperature.

35. A method according to claim 33, wherein the mixing is effected at 20–90° C.

36. A method according to claim 33, wherein the mixing is effected at 40–60° C.

37. An electrolyte comprising at least one tetrakisfluoroalkylborate of general formula (I) according to claim 1, or at least one mixture thereof further comprising at least one polymer.

38. An electrolyte according to claim 37, wherein the concentration of the tetrakisfluoroalkylborate salt(s) in the electrolyte is from 0.01 to 3 mol/l.

39. An electrolyte according to claim 37, wherein the concentration of the tetrakisfluoroalkylborate salt(s) in the electrolyte is 0.01–2 mol/l.

40. An electrolyte according to claim 37, wherein the concentration of the tetrakisfluoroalkylborate salt(s) in the electrolyte is 0.1–1.5 mol/l.

41. A primary battery comprising at least one tetrakisfluoroalkylborate of general formula (I) according to claim 1 or at least one mixture thereof further comprising at least one polymer.

42. A secondary battery comprising at least one tetrakisfluoroalkylborate of general formula (I) according to claim 1 or at least one mixture thereof further comprising at least one polymer.

43. A capacitor comprising at least one tetrakisfluoroalkylborate of general formula (I) according to claim 1 or at least one mixture thereof further comprising at least one polymer.

44. A supercapacitor comprising at least one tetrakisfluoroalkylborate of general formula (I) according to claim 1 or at least one mixture thereof further comprising at least one polymer.

45. A galvanic cell comprising at least one tetrakisfluoroalkylborate of general formula (I) according to claim 1 or at least one mixture thereof further comprising at least one polymer.

46. An electrolyte, a primary battery, a secondary battery, a capacitor, a supercapacitor, or a galvanic cell comprising at least one tetrakisfluoroalkylborate salt according to claim 1, or a mixture comprising at least one tetrakisfluoroalkylborate salt and at least one polymer, optionally in combination with other conducting salts and/or additives.

47. A tetrakisfluoroalkylborate salt of formula (I)

$$M^{n+}([BR_4]^-)_n \quad (I)$$

wherein

M$^{n+}$ is a magnesium or aluminum cation;

each of the ligands R are the same and straight-chained or branched, representing $(C_xF_{2x+1})$, with $1 \leq x \leq 8$; and n=1, 2 or 3.

48. A tetrakisfluoroalkylborate salt of formula (I)

$$M^{n+}([BR_4]^-)_n \quad (I)$$

wherein

M$^{n+}$ is an organic cation;

each of the ligands R are the same and straight-chained or branched, representing $(C_xF_{2x+1})$, with $1 \leq x \leq 8$; and n=1, 2 or 3.

49. A tetrakisfluoroalkylborate salt of formula (I)

$$M^{n+}([BR_4]^-)_n \quad (I)$$

wherein

M$^{n+}$ is a heteroaromatic cation of general formulas (II) to (IX):

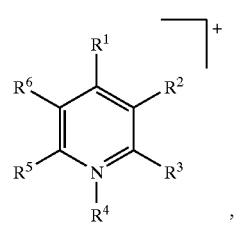

(II)

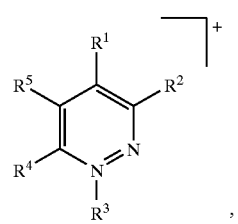

(III)

-continued

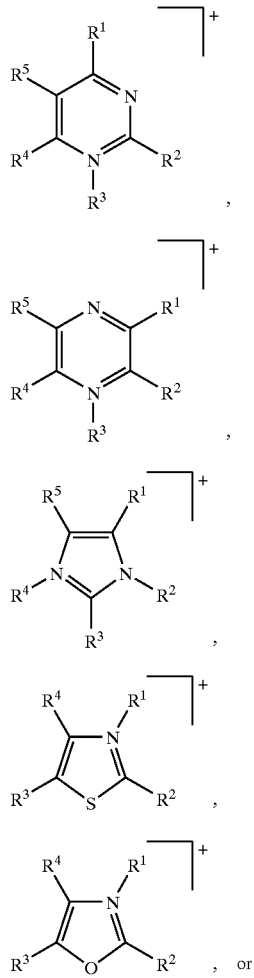

(IV), (V), (VI), (VII), (VIII), or

-continued

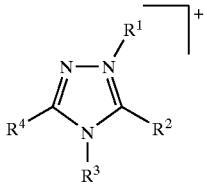

(IX)

wherein the residues $R^1$ to $R^6$, each of which is the same or different, and optionally two of the residues $R^1$ to $R^6$ together, represent H, a halogen, or a $C_{1-8}$ alkyl residue optionally substituted by F, Cl, $N(C_aF_{(2a+1-b)}H_b)_2$, $O(C_aF_{(2a+1-b)}H_b)$, $SO_2(C_aF_{(2a+1-b)}H_b)$, or $C_aF_{(2a+1-b)}H_b$ wherein $1 \leq a \leq 6$, and $0 \leq b \leq 2a+1$;

each of the ligands R are the same and straight-chained or branched, representing $(C_xF_{2x+1})$, with $1 \leq x \leq 8$; and n=1, 2 or 3.

50. A mixture comprising 5–99 wt. % of at least one tetrakisfluoroalkylborate salt of formula (I)

$$M^{n+}([BR_4]^-)_n \qquad (I)$$

$M^{n+}$ is a univalent, bivalent, or trivalent cation, each of the ligands R are the same and straight-chained or branched, representing $(C_xF_{2x+1})$, with $1 \leq x \leq 8$; and n=1, 2 or 3; and 95–1 wt. % of at least one polymer.

* * * * *